United States Patent
Ishiyama (10) Patent No.: US 7,440,547 B2
(45) Date of Patent: Oct. 21, 2008

(54) CT SCANNER

(75) Inventor: Fumio Ishiyama, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/402,845

(22) Filed: Apr. 13, 2006

(65) Prior Publication Data

US 2006/0233297 A1   Oct. 19, 2006

(30) Foreign Application Priority Data

Apr. 15, 2005   (JP) .............................. 2005-118768

(51) Int. Cl.
*H05G 1/10* (2006.01)
*H05G 1/22* (2006.01)
*H05G 1/00* (2006.01)

(52) U.S. Cl. .......................... 378/101; 378/106; 378/9

(58) Field of Classification Search .................. 378/1, 378/9, 15, 19, 101, 106, 109–119, 4
See application file for complete search history.

(56) References Cited

U.S. PATENT DOCUMENTS

| | | | | |
|---|---|---|---|---|
| 3,263,151 A * | 7/1966 | Boeker | ........................ | 363/135 |
| 4,303,830 A * | 12/1981 | Heinzelmann et al. | ......... | 378/9 |
| 4,384,359 A * | 5/1983 | Franke | ........................... | 378/9 |
| 4,991,190 A | 2/1991 | Mori | | |
| 4,995,069 A * | 2/1991 | Tanaka | ......................... | 378/200 |
| 6,215,850 B1 * | 4/2001 | Blake et al. | .................. | 378/114 |
| 6,556,651 B1 * | 4/2003 | Thomson et al. | .............. | 378/65 |
| 6,816,573 B2 * | 11/2004 | Hirano et al. | ................ | 378/114 |
| 7,039,153 B2 * | 5/2006 | Bruder et al. | ................... | 378/9 |
| 2003/0076921 A1 * | 4/2003 | Mihara et al. | ................... | 378/4 |
| 2004/0213371 A1 | 10/2004 | Bruder et al. | | |

FOREIGN PATENT DOCUMENTS

JP         2-52640         2/1990

* cited by examiner

*Primary Examiner*—Irakli Kiknadze
(74) *Attorney, Agent, or Firm*—Oblon, Spivak, McClelland, Maier & Neustadt, P.C.

(57) ABSTRACT

A CT scanner which collects X-ray projection data of a subject and which generates an image in the subject from the projection data, the CT scanner includes tubes which emit X-rays and which include grids to switch emission and stoppage of the X-rays, a unit which generates a high voltage to be supplied to the tubes, a cable which sends the high voltage to each of the tubes, circuits which change potentials of the grids arranged in the tubes, respectively, a control unit which controls the circuits to switch the emission and the stoppage of the X-rays in a pulse manner while the tubes rotate around the subject, detectors arranged to face the tubes, respectively, and a unit which validates an output signal from the detector facing the tube emitting the X-rays and which invalidates an output signal from the detector facing the tube stopping the emission of the X-rays.

24 Claims, 7 Drawing Sheets

CT SCANNER

CROSS-REFERENCE TO RELATED APPLICATIONS

This application is based upon and claims the benefit of priority from prior Japanese Patent Application No. 2005-118768, filed Apr. 15, 2005, the entire contents of which are incorporated herein by reference.

BACKGROUND OF THE INVENTION

1. Field of the Invention

The present invention relates to a CT scanner including a plurality of sets of X-ray tubes and X-ray detectors.

2. Description of the Related Art

In a CT scanner of a rotate/rotate (R-R) system, a set of an X-ray tube and an X-ray detector are arranged to face each other on a rotary stand. Moreover, in this CT scanner, the X-ray tube and the X-ray detector obtain projection data while rotating around a subject, and an image in the subject is reconstructed from the projection data.

In diagnosis of an internal organ such as the heart which moves quickly, scanning needs to be completed in a short time in order to obtain a clear image. It is effective to increase a rotation speed of the stand in order to realize such scanning in the R-R system. However, when the rotation speed of the stand is raised, a centrifugal force rises in proportion to a square of the rotation speed. Therefore, in general, 0.3 second/rotation degree is a limitation.

Consequently, a technology is disclosed in Jpn. Pat. Appln. KOKAI Publication No. 2-52640 in which a plurality of sets of X-ray tubes and X-ray detectors are mounted, and these simultaneously collect the projection data, so that a scanning time is reduced without raising the rotation speed.

However, when high-voltage devices are mounted on the plurality of X-ray tubes, a weight of the stand increases, and this lengthens the time required from a time when the rotation of the stand is started until the rotation is stabilized. Since a plurality of X-ray high-voltage devices are simultaneously operated, power supplied to a rotary portion of the stand increases, and the life of a slip ring shortens. Since output voltages of the X-ray high-voltage devices fluctuate, a difference is made in tube voltages of the plurality of X-ray tubes, and an artifact might be generated.

Furthermore, since the plurality of X-ray tubes simultaneously emit X-rays from different directions, an image blurs under influences of scattered rays.

BRIEF SUMMARY OF THE INVENTION

Such circumstances have demanded that high-speed scanning should be performed by use of a plurality of sets of X-ray tubes and X-ray detectors in order to obtain a clear image without using any X-ray high-voltage device.

According to a first aspect of the present invention, there is provided a CT scanner which collects X-ray projection data of a subject and which generates an image in the subject from the projection data, the CT scanner comprising: a plurality of X-ray tubes which emit X-rays and which include grids to switch emission and stoppage of the X-rays; a high-voltage generation unit which generates a high voltage to be supplied to the X-ray tube; a high-voltage cable which sends the high voltage to each of the plurality of X-ray tubes; a plurality of grid control circuits which change potentials of the grids arranged in the plurality of X-ray tubes, respectively; a control unit which controls the grid control circuits to switch the emission and the stoppage of the X-rays in a pulse manner while the X-ray tubes rotate around the subject; a plurality of X-ray detectors arranged to face the plurality of X-ray tubes, respectively; and a unit which validates an output signal from the X-ray detector facing the X-ray tube emitting the X-rays and which invalidates an output signal from the X-ray detector facing the X-ray tube stopping the emission of the X-rays.

According to a second aspect of the present invention, there is provided a CT scanner which collects X-ray projection data of a subject and which generates an image in the subject from the projection data, the CT scanner comprising: a plurality of X-ray tubes which emit X-rays and which include grids to switch emission and stoppage of the X-rays; a high-voltage generation unit which generates a high voltage to be supplied to the X-ray tube; a high-voltage cable which sends the high voltage to each of the plurality of X-ray tubes; a plurality of grid control circuits which change potentials of the grids arranged in the plurality of X-ray tubes, respectively; and a control unit which controls the grid control circuits to switch the emission and the stoppage of the X-rays in a pulse manner while the X-ray tubes rotate around the subject.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

There will be described hereinafter one embodiment of the present invention with reference to the drawings.

Figure 1:
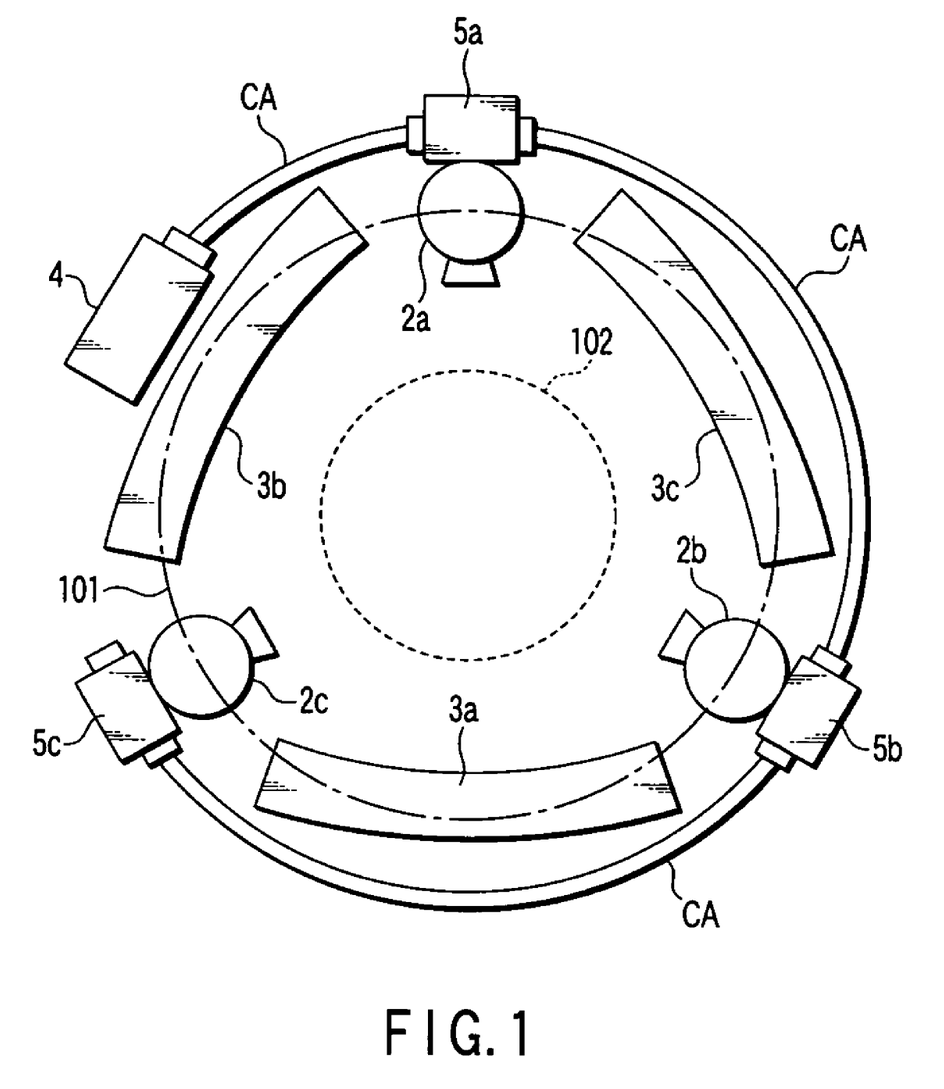
FIG. 1 is a diagram showing an arrangement of X-ray tubes and X-ray detectors in a CT scanner of one embodiment of the present invention.
Figure 2:
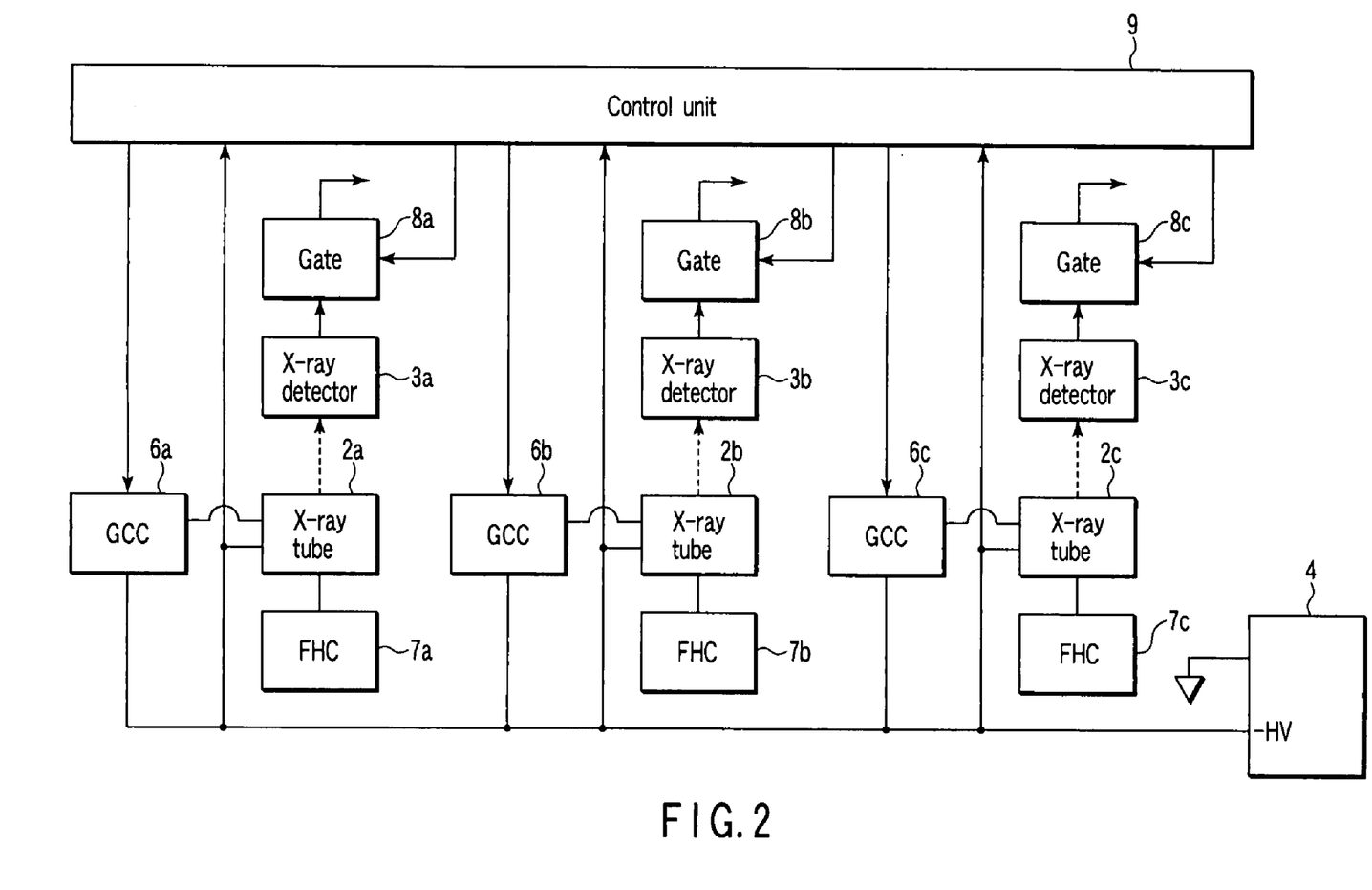
FIG. 2 is a block diagram showing an electric constitution of the CT scanner.

FIG. 1 is a diagram showing an arrangement of X-ray tubes and X-ray detectors in a CT scanner in the present embodiment. FIG. 2 is a block diagram showing an electric constitution of the CT scanner.

The CT scanner includes: X-ray tubes 2a, 2b, and 2c; X-ray detectors 3a, 3b, and 3c; a high-voltage device 4; high-voltage connectors 5a, 5b, and 5c; grid control circuits (GCC) 6a, 6b, and 6c; filament heating circuits (FHC) 7a, 7b, and 7c; gates 8a, 8b, and 8c; and a control unit 9.

The X-ray tubes 2a, 2b, and 2c, the X-ray detectors 3a, 3b, and 3c, the high-voltage device 4, and the high-voltage connectors 5a, 5b, and 5c are all mounted on a rotary stand. The X-ray tubes 2a, 2b, and 2c are arranged at intervals of 120 degrees on a circumferential rotation track 101 shown by a one-dot chain line in FIG. 1. The X-ray detectors 3a, 3b, and 3c are arranged on the circumferential rotation track 101 and face the X-ray tubes 2a, 2b, and 2c, respectively, across a space 102 located inside the circumferential track 101. It is to be noted that a subject is arranged in the space 102.

The high-voltage device 4 is connected to the high-voltage connectors 5a, 5b, and 5c by one high-voltage cable CA. The X-ray tubes 2a, 2b, and 2c are attached to the high-voltage connectors 5a, 5b, and 5c, respectively. The high-voltage device 4 supplies high voltages to the X-ray tubes 2a, 2b, and 2c via the high-voltage connectors 5a, 5b, and 5c, respectively. The grid control circuits 6a, 6b, and 6c are built in the high-voltage connectors 5a, 5b, and 5c. The grid control circuits 6a, 6b, and 6c control grid potentials of the X-ray tubes 2a, 2b, and 2c by use of the high voltages supplied from the high-voltage device 4 to the high-voltage connectors 5a, 5b, and 5c.

The gates 8a, 8b, and 8c pass or shut off output signals of the X-ray detectors 3a, 3b, and 3c, respectively.

The control unit 9 controls the grid control circuits 6a, 6b, and 6c so that the X-ray tubes 2a, 2b, and 2c operate in time division. The control unit 9 controls the gates 8a, 8b, and 8c to pass the only output signal of the X-ray detector facing the X-ray tube which emits X-rays. Furthermore, the control unit 9 monitors currents flowing into the X-ray tubes 2a, 2b, and 2c, respectively, and executes control so that the X-ray tube having a trouble is not used.

Figure 3:
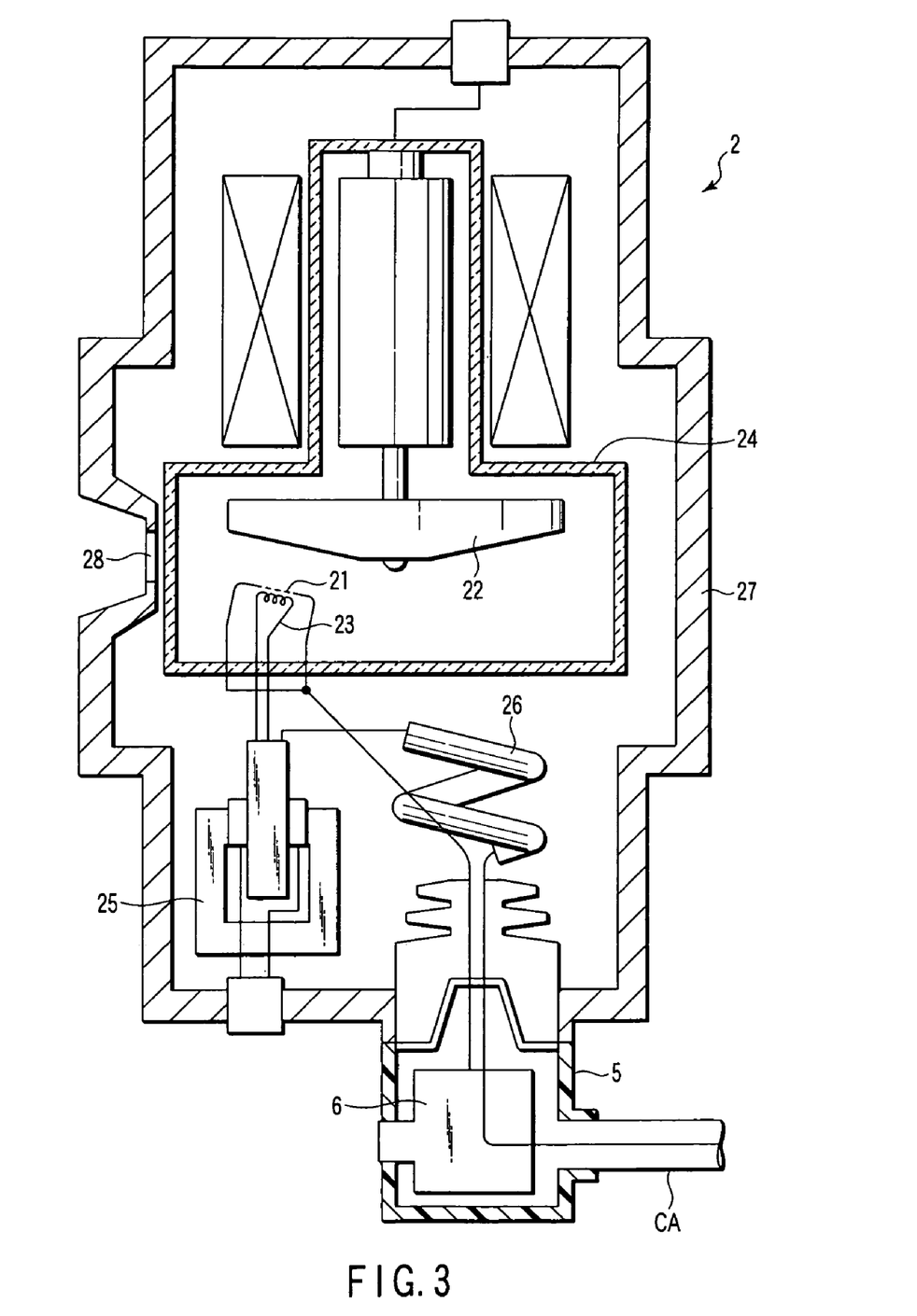
FIG. 3 is a partly broken diagram of an appearance of the X-ray tube and a grid control circuit shown in FIG. 1.
Figure 4:
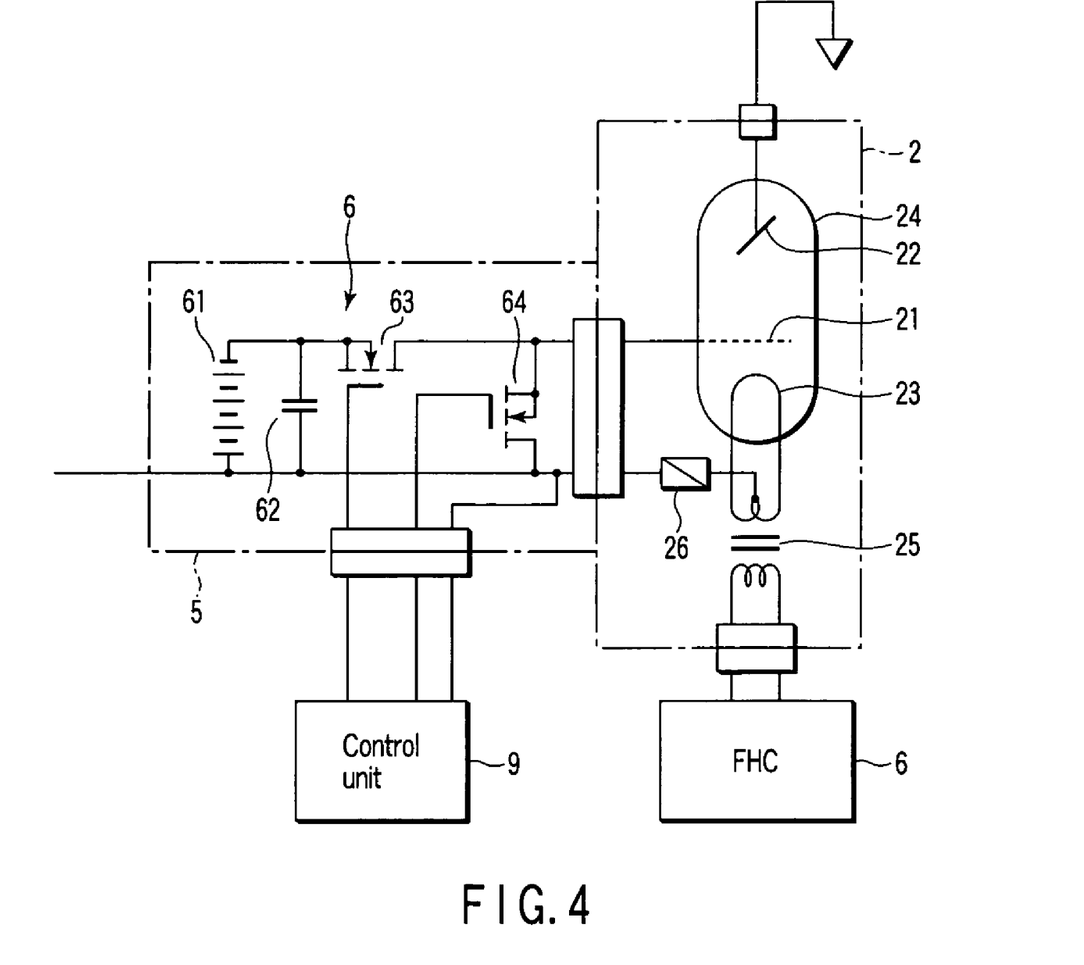
FIG. 4 is a circuit diagram showing a constitution of the X-ray tube and the grid control circuit shown in FIG. 1.

FIG. 3 is a partly broken diagram of an appearance of the X-ray tubes 2a, 2b, and 2c and the high-voltage connectors 5a, 5b, and 5c. FIG. 4 is a circuit diagram showing a constitution of the X-ray tubes 2a, 2b, and 2c and the grid control circuits 6a, 6b, and 6c. It is to be noted that the X-ray tubes 2a, 2b, and 2c have the same constitution, the high-voltage connectors 5a, 5b, and 5c have the same constitution, and the grid control circuits 6a, 6b, and 6c have the same constitution. Therefore, FIGS. 3 and 4 show only constitutions of one set of the X-ray tube, the high-voltage connector, and the grid control circuit. Moreover, the X-ray tubes 2a, 2b, and 2c, the high-voltage connectors 5a, 5b, and 5c, and the grid control circuits 6a, 6b, and 6c are shown as an X-ray tube 2, a high-voltage connector 5, and a grid control circuit 6, respectively.

The X-ray tube 2 includes a grid 21, an anode 22, a cathode 23, an insertion tube 24, a filament transformer 25, a high-voltage fuse 26, and a tube container 27.

The grid 21, the anode 22, and the cathode 23 are contained in the insertion tube 24. The insertion tube 24, the filament transformer 25, and the high-voltage fuse 26 are contained in the tube container 27.

A high voltage supplied to the high-voltage connector 5 via the high-voltage cable CA is guided to the X-ray tube 2 through the high-voltage connector 5. In the X-ray tube 2, the high voltage is applied to a center tap of a secondary wound wire of the filament transformer 25 via the high-voltage fuse 26. Accordingly, a current is generated in the cathode 23. The anode 22 is grounded, and an accelerated electron is released from the cathode 23 toward the anode 22. Moreover, when the electron collides with the anode 22, the X-ray is emitted from the anode 22. The X-rays are emitted out of the tube container 27 from an emission port 28 formed in the tube container 27. The anode 22 is set to a ground potential, and a negative high voltage is applied to the cathode 23 in order to improve a cooling efficiency of the anode 22.

The grid 21 is arranged between the anode 22 and the cathode 23. The application of the negative voltage to the grid 21 by the grid control circuit 6 is turned on/off. The grid 21 inhibits the anode 22 from being reached by the electron released from the cathode 23, when the negative voltage is applied. Accordingly, the emission of the X-rays are turned off.

The filament transformer 25 is heated by an alternating voltage output by the grid control circuit 6 to control the current flowing through the cathode 23, that is, a tube current. The high-voltage fuse 26 is fused by an excessive current to shut off the current to the cathode 23. Since the high-voltage fuse 26 is constituted by containing elements in a spiral insulating container, a sufficient cut-off voltage is obtained with a small space.

The grid control circuit 6 includes a high-voltage power supply 61, a capacitor 62, and semiconductor switches 63, 64.

The high-voltage power supply 61 generates a high negative voltage to be applied to the grid 21 of the X-ray tube 2. The negative voltage is, for example, about −1,000 to −3,000 V. The capacitor 62 is connected in parallel with the high-voltage power supply 61, and a peak current flowing at a time when the X-rays are turned off reduces a load applied to the high-voltage power supply 61. The semiconductor switch 63 turns on in a period when the X-ray emission is turned off, and applies an output voltage of the high-voltage power supply 61 to the grid 21. The semiconductor switch 64 turns on in a period when the X-ray emission from the X-ray tube 2 is turned on, and sets the voltage of the grid 21 to zero. The semiconductor switches 63, 64 are turned on and off in response to a control signal output from the control unit 9. Typical examples of devices usable as the semiconductor switches 63, 64 include a power MOS-FET. However, as the semiconductor switches 63, 64, another type of device such as an IGBT or a bipolar transistor is applicable.

There will be described an operation of the CT scanner constituted as described above.

In a case where this CT scanner performs scanning, when the rotary stand rotates, the X-ray tubes 2a, 2b, and 2c and the X-ray detectors 3a, 3b, and 3c simultaneously rotate on the rotation track 101. The X-ray tubes 2a, 2b, and 2c and the X-ray detectors 3a, 3b, and 3c have a rotation speed of, for example, about 0.4 second/once.

Figure 5:
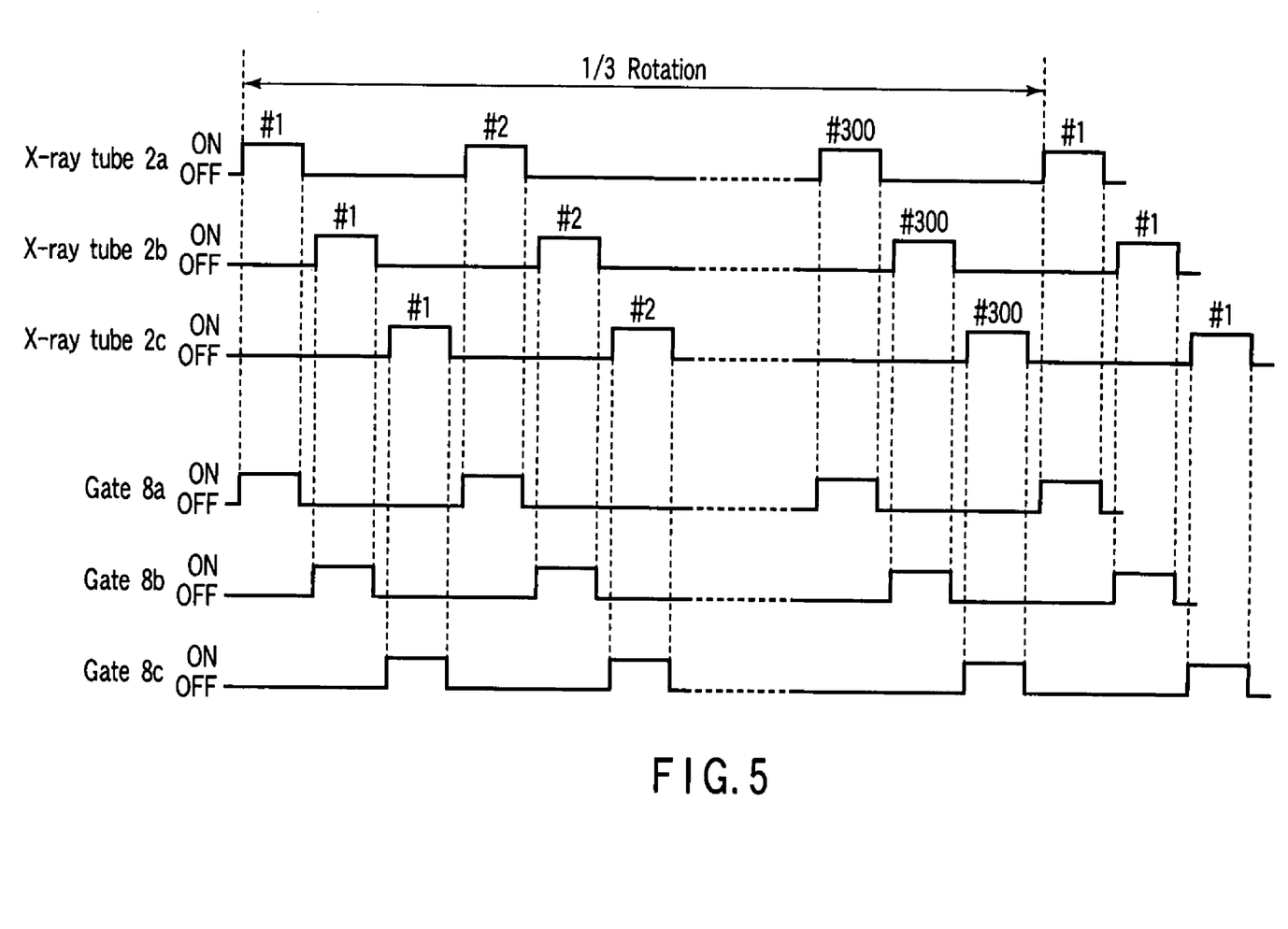
FIG. 5 is a diagram showing an operation timing of each X-ray tube shown in FIG. 1.

When the X-ray tubes 2a, 2b, and 2c rotate, the control unit 9 controls the grid control circuits 6a, 6b, and 6c so that the X-ray tubes 2a, 2b, and 2c sequentially operate every certain period as shown in FIG. 5. The grid control circuits 6a, 6b, and 6c usually apply the negative voltages to the grids 21 of the X-ray tubes 2a, 2b, and 2c, and inhibit the emission of the X-rays. Moreover, the grid control circuits 6a, 6b, and 6c set a grid voltage to zero, and emit the X-rays in an only certain period when the turning-on is instructed in a sequence shown in FIG. 5 by the control unit 9.

The X-rays emitted from the X-ray tube 2a mainly enters the X-ray detector 3a which faces this X-ray tube 2a. However, a part (scattered rays) of the X-rays irregularly reflected by the subject arranged in the space 102 also enter the other X-ray detectors 3b, 3c. This also applies even in a case where the X-ray tube 2b or 2c emits the X-rays. The scattered rays remarkably impair clearness of a reconstructed image. To solve the problem, the control unit 9 controls the gates 8a, 8b, and 8c to pass the only output from the X-ray detector which faces the operated X-ray tube. That is, as shown in FIG. 5, when, for example, the X-ray tube 2a operates, the control unit opens the gate 8a, and closes the gates 8b, 8c.

A pulse rate of the control signal supplied from the control unit 9 to each of the X-ray tubes 2a, 2b, and 2c, that is, a period to turn on and off each of the X-ray tubes 2a, 2b, and 2c is determined in accordance with the number of projection data (view number) to be collected per 360 degrees. For example, assuming that there are 900 views per 360 degrees, as shown in FIG. 5, each of the X-ray tubes 2a, 2b, and 2c may be turned on 300 times while the rotary stand rotates ⅓.

Additionally, the X-ray tubes 2a, 2b, and 2c retain electric discharge in the end of a life. In a case where one of the X-ray tubes 2a, 2b, and 2c is brought into such abnormal state, projection data required for reconstruction cannot be correctly collected in the above-described operation. Therefore, the X-ray tube brought into the abnormal state needs to be changed.

In the present embodiment, the CT scanner has a function of continuing its operation by use of two remaining X-ray tubes until the X-ray tube brought into the abnormal state is changed under such situations. There will be described hereinafter an operation by this function.

In the X-ray tube brought into the abnormal state as described above, the high-voltage fuse 26 is fused. Accordingly, any tube current does not flow in the X-ray tube brought into the abnormal state, and abnormal X-ray emission is prevented from being generated.

On the other hand, any current by the high voltage generated by the high-voltage device 4 does not flow into the X-ray tube in which the high-voltage fuse 26 is fused. The control unit 9 monitors the current which flows into each of the X-ray tubes 2a, 2b, and 2c, and judges which one of the X-ray tubes 2a, 2b, and 2c has been brought into the abnormal state based on a fact that any current does not flow into the tube as described above.

Figure 6:
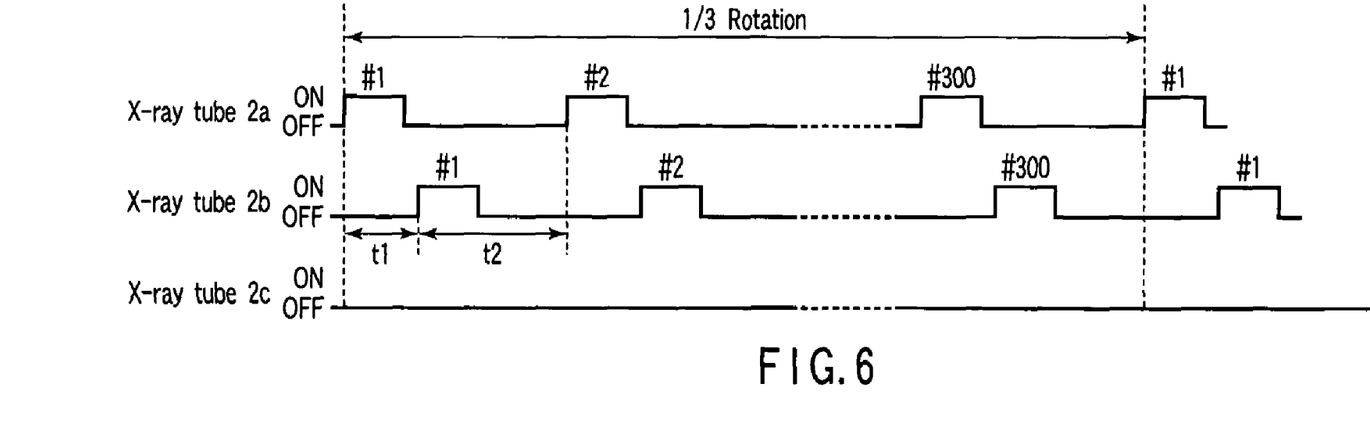
FIG. 6 is a diagram showing a first example of the operation timing of each X-ray tube shown in FIG. 1 at a time when one of the X-ray tubes of FIG. 1 is brought into an abnormal state.

Moreover, the control unit 9 constantly turns off the X-ray tube brought into the abnormal state, and the gate forming a pair with this X-ray tube, and turns on and off two other X-ray tubes and the corresponding gates. At this time, the control unit 9 sets a timing to turn on and off two normal X-ray tubes and the corresponding gates to be the same as that at a normal time as shown in FIG. 6. It is to be noted that FIG. 6 shows operation timings of the X-ray tubes 2a, 2b, and 2c in a state in which the X-ray tube 2c is brought into the abnormal state. In this case, since two normal X-ray tubes and the corresponding gates are controlled in the same manner as in the normal time, the processing of the control unit 9 is facilitated. However, since intervals t1, t2 of the X-ray emission differ, unevenness is generated in intervals of collection of the projection data, and a resolution might drop.

Figure 7:
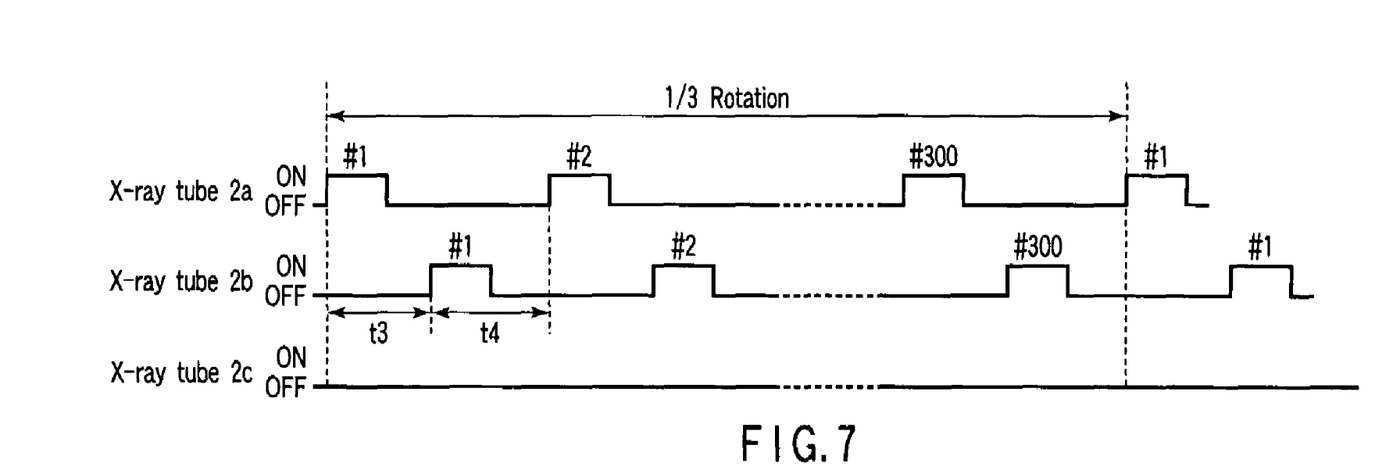
FIG. 7 is a diagram showing a second example of the operation timing of each X-ray tube shown in FIG. 1 at a time when one of the X-ray tubes of FIG. 1 is brought into the abnormal state.

Therefore, the control unit 9 may set the timing to turn on and off two normal X-ray tubes and the corresponding gates to be different from the timing at the normal time so that an X-ray emission interval t3 becomes equal to t4 as shown in FIG. 7. In this case, the processing of the control unit 9 becomes complicated. However, since the interval of the collection of the projection data becomes uniform, any drop is not generated in the resolution.

Figure 8:
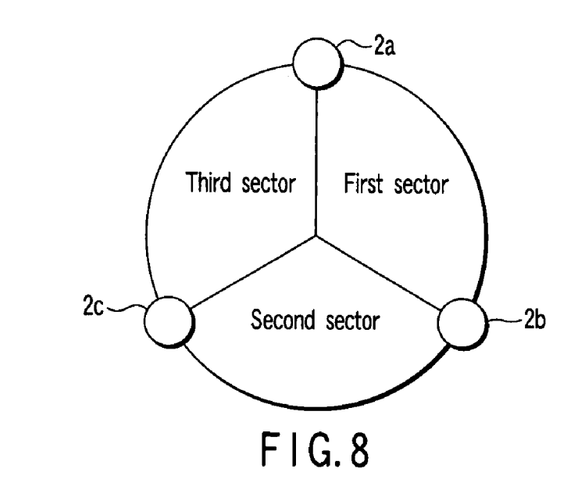
FIG. 8 is a diagram showing definitions of first, second, and third sectors.
Figure 9:
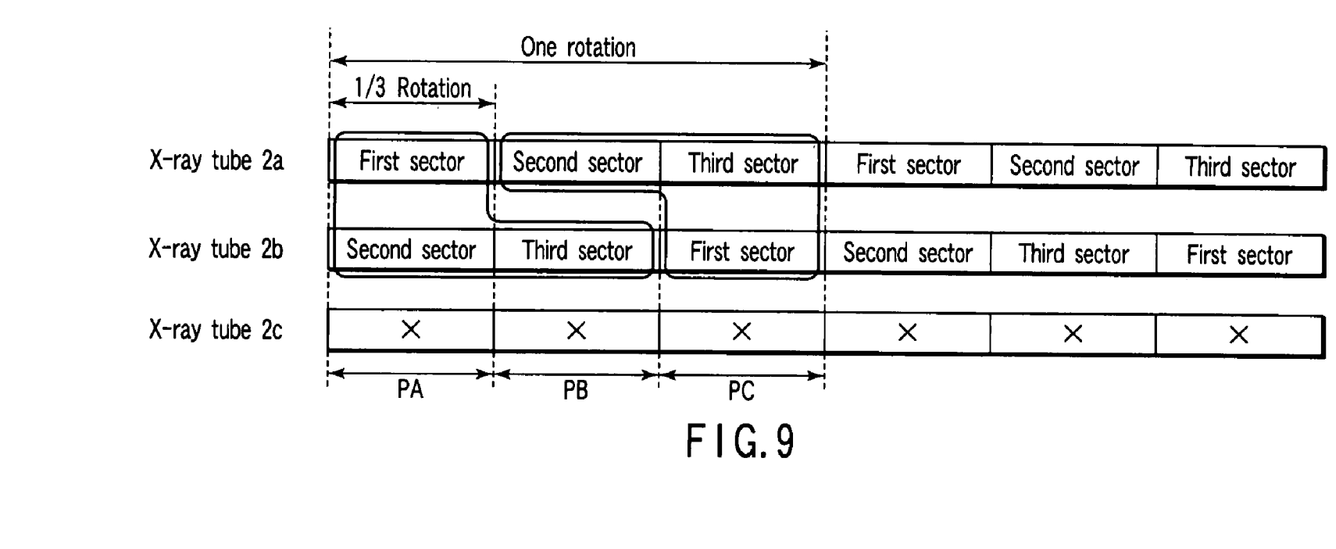
FIG. 9 is a diagram showing a change of a scanning region of each X-ray tube of FIG. 1 at a time when one of the X-ray tubes of FIG. 1 is brought into the abnormal state.

In addition, while the rotary stand rotates ⅓, the projection data collected by each of two normal X-ray tubes remains to be 300 views, and a scanning angle remains to be 120 degrees. Therefore, the projection data of 240 degrees, 600 views can only be collected in this period. Specifically, first, second, and third sectors are defined with respect to positions of the X-ray tubes 2a, 2b, and 2c in a certain time as shown in FIG. 8, and it is assumed that the X-ray tube 2c is brought into the abnormal state. At this time, as shown in FIG. 9, in a period PA in which the rotary stand rotates ⅓ next, the first and second sectors are scanned by the X-ray tubes 2a, 2b, respectively, but the third sector is not scanned.

However, in a period PB in which the rotary stand rotates ⅓ subsequently to the period PA, the third sector is scanned by the X-ray tube 2b. Therefore, when an output signal of the X-ray detector 3a in the period PA and that of the X-ray detector 3b in the period PB are obtained as one set, the projection data for 360 degrees can be obtained. In a period PC which is subsequent to the period PB and in which the rotary stand rotates ⅓, the third and first sectors are scanned by the X-ray tubes 2a, 2b, respectively, but the second sector is not scanned. However, the second sector is scanned by the X-ray tube 2a in the period PB. Therefore, assuming that output signals of the X-ray detector 3a in the periods PB and PC and an output signal of the X-ray detector 3b in the period PC are obtained as one set, the projection data for 360 degrees can be obtained.

As described above, unlike the normal time, the projection data for 360 degrees cannot be collected while the rotary stand rotates ⅓. However, while the rotary stand rotates once, the projection data for 360 degrees can be collected twice.

Even when one of the X-ray tubes 2b, 2c is brought into the abnormal state, it is possible to collect the projection data required for the reconstruction by the above-described way of thinking.

As described above, according to the present embodiment, while the rotary stand rotates ⅓, the projection data for 360 degrees, that is, one rotation can be acquired. Therefore, a scanning time is reduced to ⅓ of the stand rotation time, and high-speed scanning can be performed.

In the present embodiment, since the X-ray tubes 2a, 2b, and 2c are operated in time series, each of the X-ray tubes 2a, 2b, and 2c can be operated by a high voltage output from one high-voltage device 4. Therefore, it is possible to avoid various disadvantages generated in a case where a plurality of X-ray high-voltage devices are arranged.

In the present embodiment, since the X-ray tubes 2a, 2b, and 2c are operated in time series, the influences of scattered rays can be reduced, and it is possible to acquire the projection data effective for obtaining a clear image. Further in the present embodiment, since the output of the X-ray detector facing the halted X-ray tube is shut off by the gate, the influences of the scattered rays can be substantially eliminated, and this further contributes to improvement of definition of the image.

In addition, in an X-ray diagnosis device for a circulatory organ, pulse X-rays have heretofore been generated by a method of controlling the grid of the X-ray tube in the same manner as in the present embodiment, but a pulse rate is about 7.5 to 30 pulses/second. On the other hand, a pulse rate required in the present embodiment is about several thousands of pulses/second. If a wiring line length from the grid control circuit 6 to the X-ray tube 2 is long, a grid voltage waveform gets dull owing to a floating capacity of a wiring line, and it is difficult to realize the above-described high pulse rate. However, according to the present embodiment, the grid control circuit 6 is incorporated in the high-voltage connector 5. Therefore, the above-described disadvantage can be avoided, and the high pulse rate can be realized. Even when the grid control circuit 6 is arranged in the tube container 27, a similar effect can be obtained. However, temperature rises in the tube container 27, and the semiconductor switches 63, 64 are generally vulnerable to heat. Therefore, reliability drops. In consequence, it is optimum to incorporate the grid control circuit 6 in the high-voltage connector 5 as in the above embodiment.

On the other hand, a typical X-ray tube does not contain any filament transformer. Therefore, the high voltage generated in the filament transformer arranged externally for the X-ray tube has heretofore been supplied to the X-ray tube by a high-voltage cable. When such structure is applied to the present embodiment, three pairs of filament transformers and X-ray tubes are arranged. Therefore, the high-voltage cable needs to have at least three core wires. However, according to the present embodiment, the filament transformer 25 is contained in the X-ray tube 2. Therefore, the high-voltage cable may have one core wire common to three X-ray tubes 2a, 2b, and 2c. Further in the present embodiment, a diameter of the high-voltage cable CA can be reduced, and a structure of the high-voltage connector 5 can be simplified as compared with a case where a high-voltage cable having a multiplicity of cores is used.

Additionally, as to the typical X-ray tube, since a high voltage is applied to one node of the filament transformer, the other node has a potential corresponding to a filament voltage with respect to the grid. The same function occurs as that in a case where a voltage having a polarity opposite to that of the filament is applied to the grid. Therefore, the tube current changes with the filament voltage, and this is a cause for fluctuations of an X-ray intensity. The fluctuations of the X-ray intensity are averaged in a case where a picture is taken by the X-ray diagnosis device or in a CT scanner which continuously generates X-rays from one X-ray tube and which has a comparatively low data collecting speed, and any problem is not generated. However, when pulse X-rays are used, and the rate of the rays increases as in the present embodiment, the fluctuations of the X-ray intensity cannot be ignored. In the present embodiment, since the high voltage is applied to the center tap arranged in the secondary wound wire of the filament transformer 25, it is possible to reduce the fluctuations of the X-ray intensity by an influence of the alternating voltage output by the filament heating circuit 7.

Furthermore, according to the present embodiment, even when one of the X-ray tubes 2a, 2b, and 2c is brought into the abnormal state, the operation can be continued.

This embodiment can be variously modified as follows.

There may be arranged two or four or more sets of X-ray tubes and X-ray detectors.

When the output of the X-ray detector facing the halted X-ray tube is not used in the image reconstruction processing or the preprocessing, the gates 8a, 8b, and 8c can be omitted.

A plurality of X-ray tubes do not have to be arranged at an equal interval: with the proviso that n X-ray tubes are preferably arranged at an equal interval of 360/n degrees in order to achieve efficient scanning as in the above embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A CT scanner which collects X-ray projection data of a subject and which generates an image of the subject from the projection data, the CT scanner comprising:

first to third X-ray tubes which emit X-rays and which include grids to switch emission and stoppage of the X-rays;

a high-voltage generation unit which generates a high voltage to be supplied to the first to third X-ray tubes;

a high-voltage cable which sends the high voltage to each of the first to third X-ray tubes, the high-voltage cable connecting the high-voltage generation unit to the first X-ray tube, the second X-ray tube, and the third X-ray tube;

a plurality of grid control circuits which change potentials of the grids and are arranged near the first to third X-ray tubes, respectively, and include semiconductor switches;

a control unit which controls the grid control circuits to switch the emission and the stoppage of the X-rays in a pulse manner while the first to third X-ray tubes rotate around the subject; and a plurality of X-ray detectors arranged to face the first to third X-ray tubes, respectively.

2. The CT scanner according to claim 1, wherein the control unit controls the grid control circuits to prevent the X-rays from being emitted simultaneously by at least two X-ray tubes.

3. The CT scanner according to claim 1, wherein the plurality of grid control circuits are arranged in the first to third X-ray tubes, respectively.

4. The CT scanner according to claim 1, further comprising:

a plurality of high-voltage connectors which connect the first to third X-ray tubes to the high-voltage cable, respectively, wherein the plurality of grid control circuits are contained in the plurality of high-voltage connectors, respectively.

5. The CT scanner according to claim 1, wherein each X-ray tube contains a filament transformer which heats a cathode of each X-ray tube.

6. The CT scanner according to claim 1, wherein the high-voltage cable has one core wire which sends the high voltage, and the first to third X-ray tubes are electrically connected to the core wire.

7. The CT scanner according to claim 1, wherein the high-voltage cable is arranged so that the first to third X-ray tubes are arranged in order along the high-voltage cable.

8. The CT scanner according to claim 1, wherein each X-ray tube contains a transformer which applies an alternating voltage to a cathode of each X-ray tube.

9. The CT scanner according to claim 1, wherein a number of a plurality of X-ray tubes is n, the plurality of X-ray tubes are arranged at intervals of 360/n degrees, and the control unit controls the plurality of X-ray tubes to emit the X-rays sequentially, and to emit the X-rays a same number of times, while the plurality of X-ray tubes are rotated through 360/n degrees.

10. The CT scanner according to claim 1, wherein each X-ray tube includes a unit which prevents an abnormal current from being introduced into a cathode of each X-ray tube.

11. The CT scanner according to claim 1, wherein the control unit detects abnormalities of the first to third X-ray tubes, respectively, and controls the grid control circuits to constantly stop abnormal X-ray tubes while switching emission and stoppage of the X-rays in other X-ray tubes in the pulse manner, and to prevent the X-rays from being emitted simultaneously by at least two X-ray tubes.

12. The CT scanner according to claim 1, wherein the high-voltage cable includes:

a first cable portion which connects the high-voltage generation unit to the first X ray tube;

a second cable portion which connects the first X ray tube to the second X ray tube; and a third cable portion which connects the second X ray tube to the third X ray tube.

13. A CT scanner which collects X-ray projection data of a subject and which generates an image of the subject from the projection data, the CT scanner comprising:

a plurality of X-ray tubes which emit X-rays and which include grids to switch emission and stoppage of the X-rays;

a high-voltage generation unit which generates a high voltage to be supplied to the plurality of X-ray tubes;

a high-voltage cable which sends the high voltage to each of the plurality of X-ray tubes;

a plurality of grid control circuits which change potentials of the grids arranged in the plurality of X-ray tubes, respectively;

a control unit which controls the grid control circuits to switch the emission and the stoppage of the X-rays in a pulse manner while the X-ray tubes rotate around the subject, and which detects abnormalities of the plurality of X-ray tubes, respectively, and controls the grid control circuits to constantly stop the abnormal X-ray tubes while switching the emission and the stoppage of the X-rays in the other X-ray tubes in the pulse manner, and to prevent the X-rays from being emitted simultaneously by at least two X-ray tubes; and a plurality of X-ray detectors arranged to face the plurality of X-ray tubes, respectively.

14. The CT scanner according to claim 13, wherein the control unit controls the grid control circuits to prevent the X-rays from being emitted simultaneously by at least two X-ray tubes.

15. The CT scanner according to claim 13, wherein the high-voltage cable connects high-voltage input portions of the plurality of X-ray tubes in parallel with an output portion of the high-voltage generation unit.

16. The CT scanner according to claim 13, wherein the plurality of X-ray tubes include first to third X-ray tubes, and the high-voltage cable includes:

a first cable portion which connects the high-voltage generation unit to the first X-ray tube;

a second cable portion which connects the first X-ray tube to the second X-ray tube; and a third cable portion which connects the second X-ray tube to the third X-ray tube.

17. The CT scanner according to claim 13, wherein the plurality of grid control circuits are arranged either in or near the plurality of X-ray tubes, respectively.

18. The CT scanner according to claim 13, further comprising:

a plurality of high-voltage connectors which connect the plurality of X-ray tubes to the high-voltage cable, respectively, wherein the plurality of grid control circuits are contained in the plurality of high-voltage connectors, respectively.

19. The CT scanner according to claim 13, wherein each X-ray tube contains a filament transformer which heats a cathode of each X-ray tube.

20. The CT scanner according to claim 13, wherein the high-voltage cable has one core wire which sends the high voltage, and the plurality of X-ray tubes are electrically connected to the core wire.

21. The CT scanner according to claim 13, wherein the high-voltage cable is arranged so that the plurality of X-ray tubes are arranged in order along the high-voltage cable.

22. The CT scanner according to claim 13, wherein each X-ray tube contains a transformer which applies an alternating voltage to a cathode of each X-ray tube.

23. The CT scanner according to claim 13, wherein a number of the plurality of X-ray tubes is n, the plurality of X-ray tubes are arranged at intervals of 360/n degrees, and the control unit controls the plurality of X-ray tubes to emit the X-rays sequentially, and to emit the X-rays a same number of times, while the plurality of X-ray tubes are rotated through 360/n degrees.

24. The CT scanner according to claim 13, wherein each X-ray tube includes a unit which prevents an abnormal current from being introduced into a cathode of each X-ray tube.

* * * * *